(12) United States Patent
Rurling et al.

(10) Patent No.: US 9,827,046 B2
(45) Date of Patent: Nov. 28, 2017

(54) FRAME FOR FIXATION OF EQUIPMENT TO THE HEAD OF A PATIENT DURING NEUROLOGICAL DIAGNOSIS, STEREOTACTIC IMAGING, THERAPY OR SURGERY

(71) Applicant: ELEKTA AB (PUBL), Stockholm (SE)

(72) Inventors: Erik Rurling, Bromma (SE); Anna Wik, Hägersten (SE); Malin Svensson, Stockholm (SE); Ivars Alksnis, Trångsund (SE); Marianne Plantz, Stockholm (SE); Mathias Stavervik, Stockholm (SE)

(73) Assignee: ELEKTA AB (PUBL), Stockholm (SE)

( * ) Notice: Subject to any disclaimer, the term of this patent is extended or adjusted under 35 U.S.C. 154(b) by 323 days.

(21) Appl. No.: 14/517,056

(22) Filed: Oct. 17, 2014

(65) Prior Publication Data

US 2015/0119902 A1 Apr. 30, 2015

(30) Foreign Application Priority Data

Oct. 31, 2013 (EP) .................................... 13191077

(51) Int. Cl.
*A61B 19/00* (2006.01)
*A61B 17/00* (2006.01)
(Continued)

(52) U.S. Cl.
CPC ............ *A61B 19/203* (2013.01); *A61B 90/14* (2016.02); *A61B 90/11* (2016.02); *A61B 2017/00911* (2013.01)

(58) Field of Classification Search
USPC .................................................. 606/59, 130
See application file for complete search history.

(56) References Cited

U.S. PATENT DOCUMENTS

| 4,612,930 A | 9/1986 | Bremer |
| 5,456,266 A | 10/1995 | Brown |

(Continued)

FOREIGN PATENT DOCUMENTS

| WO | WO 03/094769 A1 | 11/2003 |
| WO | WO 2013/011443 A1 | 1/2013 |

OTHER PUBLICATIONS

SHL Technologies, "An OEM Partner with a Medical Quality System Already in Place," 2009 Retrieved from the Internet: http://www.shl-group.com/ product/neurosurgical-equipment/>.

*Primary Examiner* — Nicole F Johnson
(74) *Attorney, Agent, or Firm* — Birch, Stewart, Kolasch & Birch, LLP

(57) ABSTRACT

A frame for fixation of equipment to the head of a patient during neurological diagnosis, therapy or surgery is adapted to enclose the head of the patient. The frame includes a number of mounting slots arranged in the frame. The mounting slots are adapted to receive a number of fixation pins adapted to fixate the frame to a bone in the head. The frame further includes two anterior longitudinal posts and two posterior longitudinal posts, extending along a longitudinal axis A, an anterior portion, adapted to be arranged at the anterior side of the head, the anterior portion interconnecting the two anterior longitudinal posts, and a posterior portion, adapted to be arranged at the posterior side of the head, the posterior portion interconnecting the two posterior longitudinal posts. The anterior longitudinal posts and the posterior longitudinal posts are interconnected with two lateral portions, adapted to extend one on each side of the head, and wherein the lateral portions are axially offset, along the longitudinal axis A, with respect to the anterior and posterior portion. A stereotactic frame system includes such a frame.

18 Claims, 2 Drawing Sheets

(51) Int. Cl.
 *A61B 90/14* (2016.01)
 *A61B 90/11* (2016.01)

(56) References Cited

U.S. PATENT DOCUMENTS

| | | | |
|---|---|---|---|
| 6,355,049 B1* | 3/2002 | Gill | A61B 90/14 |
| | | | 5/622 |
| D676,139 S | 2/2013 | Golzari | |
| D750,264 S | 2/2016 | Guarraia et al. | |
| D752,236 S | 3/2016 | Guarraia et al. | |
| D752,766 S | 3/2016 | Guarraia et al. | |
| 2002/0042619 A1* | 4/2002 | Dominguez | A61B 90/14 |
| | | | 606/130 |
| 2008/0097195 A1 | 4/2008 | Urquhart et al. | |
| 2011/0160727 A1 | 6/2011 | Arn | |
| 2012/0060847 A1 | 3/2012 | Stratton et al. | |
| 2012/0138066 A1 | 6/2012 | Akram et al. | |
| 2014/0135765 A1 | 5/2014 | Schuele et al. | |

* cited by examiner

FRAME FOR FIXATION OF EQUIPMENT TO THE HEAD OF A PATIENT DURING NEUROLOGICAL DIAGNOSIS, STEREOTACTIC IMAGING, THERAPY OR SURGERY

FILED OF THE INVENTION

The present invention relates to a frame for fixation of equipment to the head of a patient during neurological diagnosis, stereotactic imaging, therapy or surgery.

BACKGROUND OF THE INVENTION

A stereotactic frame is used for establishing a reference system to localize areas to be treated during imaging such as MRI-scanning of a head of a patient and/or for supporting instruments during neurological surgery, therapy or diagnosis. The stereotactic frame is arranged around the head and fixation pins connected to the frame are screwed into or to abutment against the bone of the skull to ensure a rigid fixation of the reference system.

One example of a stereotactic frame is shown in WO 03/094769, which is assigned to the present assignee, and which discloses a device for fixation to a patient during neurological diagnosis, therapy or surgery, in particular during MRI diagnosis. The fixation device comprises four pin support members. The four pin support members are arranged in the corners of a rectangular stereotactic frame comprising four frame parts.

Another example is shown in pending U.S. Publication No.: 20110160727, which also is assigned to the present assignee, wherein a stabilizing device adapted to be applied to a stereotactic frame is disclosed. The stabilizing device is provided with fixation pins to allow fixation of the stereotactic frame to a bone of a human or animal body part to be examined or treated, wherein the stabilizing device is adapted to stabilize a fixation pin in relation to the frame.

Although stereotactic frames designed according to the techniques presented by the present assignee in practise have been proven to work very well, there are continuously ongoing efforts to improve the performance and functionality of the stereotactic frames.

The inventors of the present invention have identified a need for an improved frame which is easy and straightforward to use, and which facilitates handling for the operator.

One object of the present invention is to provide a fixation frame with improved versatility.

Another object of the present invention is to provide a fixation frame which is optimized for fitting into small medical equipments.

Yet another object of the present invention is to provide a fixation frame which provides an easy work flow, improved comfort and safety for the patient, and improved handling for the operator.

SUMMARY OF THE INVENTION

The above-mentioned objects are achieved by the present invention according to the independent claim.

Preferred embodiments are set forth in the dependent claims.

According to a first aspect of the present invention, the frame for fixation of equipment to the head of a patient during neurological diagnosis, stereotactic imaging, therapy or surgery, comprises a number of mounting slots arranged in said frame, the mounting slots are adapted to receive a number of fixation pins adapted to fixate said frame to a bone in said head. The frame is adapted to enclose the head of the patient. The frame further comprises two anterior longitudinal posts and two posterior longitudinal posts, extending along a longitudinal axis A. Furthermore, the frame comprises an anterior portion, adapted to be arranged at the anterior side of the head, said anterior portion interconnecting said two anterior longitudinal posts, and a posterior portion, adapted to be arranged at the posterior side of the head, said posterior portion interconnecting said two posterior longitudinal posts. The anterior longitudinal posts and the posterior longitudinal posts are interconnected with two lateral portions, adapted to extend one on each side of said head, and wherein said lateral portions are axially offset, along said axis A, with respect to said anterior and posterior portions.

In other words, the frame for fixation of equipment to the head of a patient comprises a frame which runs continuously around the patients head. As mentioned above, the frame comprises two anterior longitudinal posts, one anterior portion, two posterior longitudinal posts, one posterior portion, and two lateral portions. The anterior portion, the posterior portion, and the lateral portions are extending in a direction essentially perpendicular to the anterior longitudinal posts and the posterior longitudinal posts. The anterior portion is interconnecting the anterior longitudinal posts, and the posterior portion is interconnecting the posterior longitudinal posts. A lateral portion is further arranged to interconnect each posterior longitudinal post with an anterior longitudinal post.

Furthermore, the lateral portions are axially offset, along said axis A, with respect to said anterior and posterior portions. i.e. the lateral portions are displaced along said longitudinal axis A with respect to said anterior and posterior portions. Thus, the lateral portions are adapted to extend in a transverse plane, plane B, and the anterior portion and the posterior portion are adapted to extend in another transverse plane, plane C, separated along said longitudinal axis A from said transverse plane B.

In one embodiment, the anterior portion and the posterior portion are slightly offset with respect to each other along said axis A. The anterior portion is preferably arranged superior of the posterior portion, in other words the anterior portion is arranged in a plane superior of the posterior portion. This is advantageous in that fitting the frame to different sizes of heads and different shapes of heads is facilitated.

The invention is based on the insight that it is advantageous to adapt the shape of the frame to the shape of the head, such that the play between the head of the patient and the frame is minimized. Thereby, the outer dimensions of the frame is minimized, which facilitates handling in case of diagnosis, therapy or surgery using small medical equipments, such as MRI head coils, or treatment with a gamma knife apparatus. Thus, the frame more easily fits into various medical equipments.

The two anterior longitudinal posts are adapted to be arranged one on each side of the face of the patient. The anterior portion, interconnecting the two anterior longitudinal posts, is adapted to extend over the forehead of the patient. Thereby, the face of the patient is left essentially free, and thereby e.g. treatment with an oxygen apparatus during treatment, therapy or diagnosis is facilitated.

According to one embodiment, each one of said anterior and posterior longitudinal posts comprises a superior end and an inferior end, wherein said anterior portion is interconnecting said superior ends of said anterior longitudinal posts. Thus, a first end of said anterior portion is attached to a superior end of one of said anterior longitudinal posts, and a second opposite end of said anterior portion is attached to the other one of said anterior longitudinal posts. Thereby, the face, and in particular the mouth and the nose, of the patient is left essentially free, i.e. is left open for surgical interactions.

In one embodiment said posterior portion is interconnecting said superior ends of said posterior longitudinal posts. In a similar way as mentioned above, a first end of said posterior portion is attached to a superior end of one of said posterior longitudinal posts, and a second opposite end of said posterior portion is attached to the other one of said posterior longitudinal posts. Thereby, a posterior area of the patients head is left essentially free such that the area is left open for surgical interactions.

In one embodiment said lateral portions are interconnecting said inferior ends of said anterior longitudinal posts and said posterior longitudinal posts. Thus, each one of said lateral portions extends between an inferior end of one of said anterior longitudinal posts and an inferior end of one of said posterior longitudinal posts. Thereby, by connecting the two anterior longitudinal posts at the superior ends, the two posterior longitudinal posts at the superior ends, and the anterior longitudinal posts and the posterior longitudinal posts at the inferior ends, desired areas of the patients head, such as the face and the whole side of the skull, is left open for surgical interactions. A further advantage is that the frame, and in particular the anterior portion of the frame, then may be adapted to extend over the forehead such that the frame may be fixed to a bone in said forehead.

In one embodiment said anterior portion comprises a number of mounting slots. Thereby, the frame, and in particular the anterior portion may be fixated to a bone in the forehead. The face of the patient is then left open for surgical interactions. The number of mounting slots are at least four. There may be arranged a plurality of mounting slots in the frame, however, when fixating the frame in the bone, depending on the particular case, the operator may chose not to arrange mounting pins in all of the mounting slots. A plurality of mounting slots improves versatility of the frame.

In one embodiment said posterior portion comprises a number of mounting slots. As also mentioned above, a plurality of mounting slots improves versatility of the frame.

In one embodiment said anterior portion is adapted to extend superior of the eyes of said patient. Thereby, the frame may be fixated to a bone in the forehead of the patient, which provides for a secure fixing of the frame to the bone in the head, and furthermore the face is left free, i.e. is left open for surgical interactions.

In one embodiment the lateral portions are adapted to be arranged inferior of the ears of the head of the patient. Thereby access to an area superior of the ears of the patient is facilitated. This facilitates e.g. open surgery, radiotherapy, and imaging.

In one embodiment said frame has a curved shape which is adapted to the shape of the head. Thereby, the outer dimension of the frame is minimized, such that fitting the frame into small medical equipments, such as modern tight MR coils, is facilitated.

In one embodiment, said frame is made from a composite material. However, the frame may be made from any other suitable material which is sufficiently rigid. The composite material is advantageous in that the frame will become electromagnetically inert, thereby reducing or eliminating artefacts during imaging.

In one embodiment, said anterior longitudinal posts and said anterior portion are adapted to be arranged such that the face of the patient is essentially free.

In one embodiment said frame has an outer width w, and wherein said width is approximately 24 cm. Thereby, the frame is sufficiently small and at the same time will accommodate virtually all sizes of heads whereby the versatility of the frame is improved.

In one embodiment, each one of said lateral portions comprises at least one fastening device, adapted to detachably attach said frame to a stereotactic frame system. This facilitates attachment of the frame to the stereotactic frame system.

According to another aspect, the present invention relates to a stereotactic frame system comprising a frame as described above. The stereotactic frame system comprises a frame docking device, and wherein said frame is detachably attached to said frame docking device. This provides for improved versatility of the frame. The frame may be used with many other different types of medical equipments. The frame docking device provides for easy and secure attachment of the frame in the stereotactic frame system.

In one embodiment said frame docking device comprises at least one stereotactic scale. The stereotactic scale being attached to the frame docking device is advantageous in that, in case of, or when, the frame flexes when screws are tightened, when fixing the frame to the head of the patient, the scales will not be affected. Thereby, accuracy of the stereotactic frame system is independent from any possible flex occurring in the frame when fixing the frame to the head.

In one embodiment, said frame docking device comprises at least one stereotactic scale attachment means, and wherein said stereotactic scale is attached to said attachment means. Thus the stereotactic scale may be arranged directly on the frame docking device or attached via a stereotactic scale attachment means. Thereby, versatility of the frame is improved.

BRIEF DESCRIPTION OF THE DRAWINGS

Embodiments of the invention will hereinafter be described by way of example with reference to the accompanying drawings, in which.

DETAILED DESCRIPTION OF EMBODIMENTS OF THE INVENTION

Throughout the application the word superior means a direction towards the head of a patient and inferior means a direction towards the feet of the patient, thus, a part located superior of another part is located above or on top of an inferior part.

Furthermore, the word anterior refers to a part located on or near the front of the body of the patient and the word posterior refers to a part located towards the rear of the body of the patient.

Figure 1:
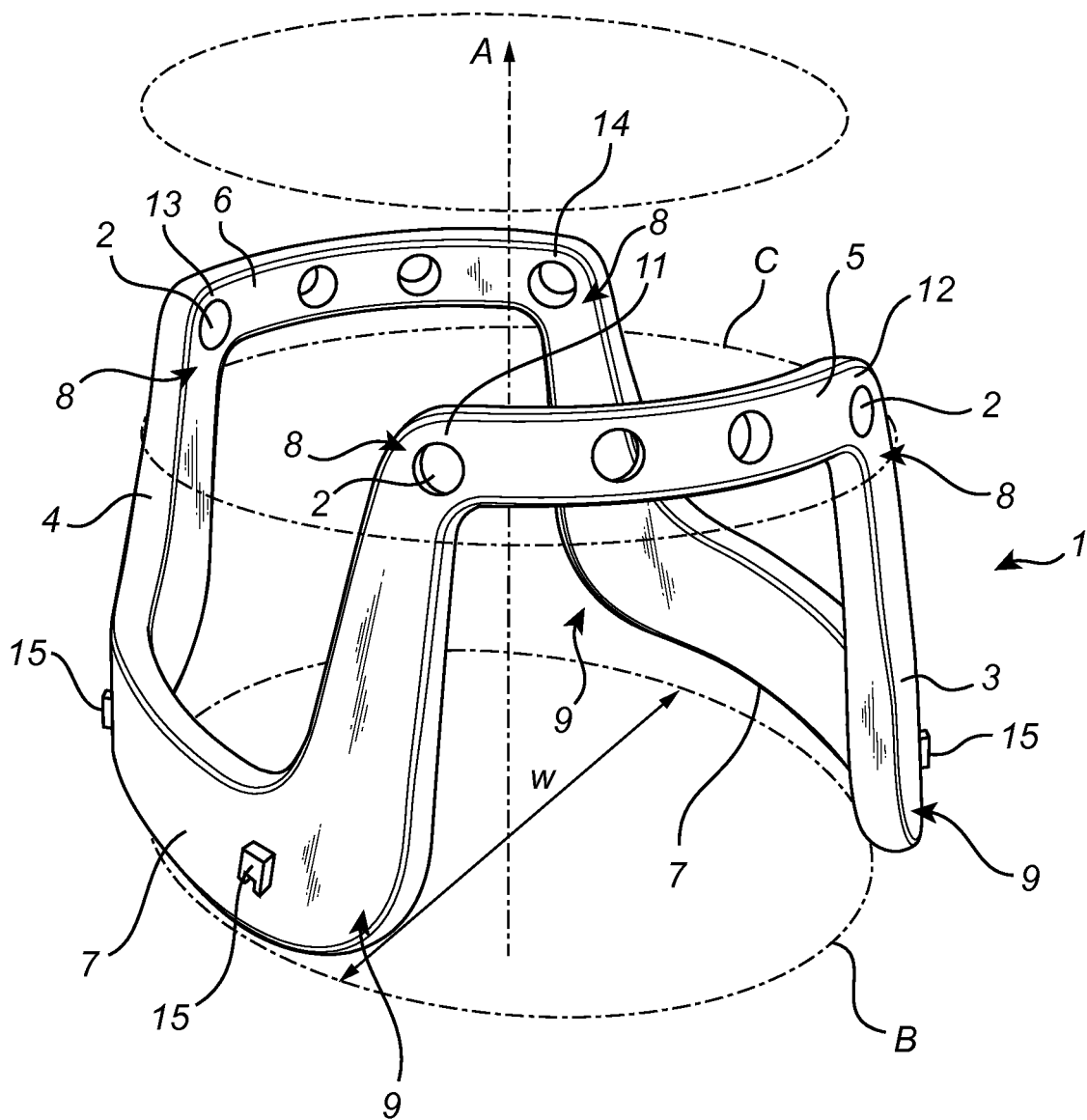
FIG. 1 shows a frame for fixation of equipment to the head of a patient during neurological diagnosis, therapy or surgery, according to one embodiment of the present invention.

Reference is first made to FIG. 1, in which is illustrated a frame 1 for fixation of equipment (not shown) to the head of a patient during neurological diagnosis, stereotactic imaging, therapy or surgery, according to one embodiment of the invention. The frame 1 comprises eight mounting slots 2 arranged in the frame 1. Naturally, any other number of mounting slots 2 may be arranged in the frame 1. The mounting slots 2 are distributed around the frame 1 such that mounting slots 2 are provided both at more anterior parts of the frame 1 and at more posterior parts of the frame 1. The mounting slots 2 are adapted to receive fixation pins (not shown) adapted to fixate the frame 1 to a bone in the head. The frame 1 is adapted to enclose the head of the patient. The frame 1 further comprises two anterior longitudinal posts 3 and two posterior longitudinal posts 4, extending along a longitudinal axis A. Furthermore, the frame 1 comprises an anterior portion 5, adapted to be arranged at the anterior side of the head, the anterior portion 5 is interconnecting the two anterior longitudinal posts 3. A posterior portion 6, adapted to be arranged at the posterior side of the head, is interconnecting the two posterior longitudinal posts 4.

As further seen in FIG. 1, the anterior longitudinal posts 3 and the posterior longitudinal posts 4 are interconnected with two lateral portions 7, adapted to extend one on each side of the head. The lateral portions 7 are axially offset, i.e. axially displaced, along the axis A, with respect to the anterior and posterior portions 5, 6. Thus, the lateral portions 7 are adapted to extend in a transverse plane, plane B, and the anterior portion 5 and the posterior portion 6 are adapted to extend in another transverse plane, plane C, separated along the longitudinal axis A from the transverse plane B. The anterior portion 5, the posterior portion 6, and the lateral portions 7 are extending in a direction essentially perpendicular to the anterior longitudinal posts 3 and the posterior longitudinal posts 4. The frame 1 is made from a composite material, preferably a electromagnetically inert composite material. Furthermore, the anterior portion 5 may be arranged superior of the posterior portion 6 along the axis A, i.e. the anterior portion 5 then being axially offset, or displaced, along axis A with respect to the posterior portion 6.

Each one of the anterior longitudinal posts 3 and the posterior longitudinal posts 4 comprises a superior end 8 and an inferior end 9. Naturally, the superior ends 8 are adapted to be arranged superior to the inferior ends 9 with respect to the patient. Furthermore, in the embodiment illustrated in FIG. 1, the anterior portion 5 is interconnecting the superior ends 8 of the anterior longitudinal posts 3. Thus, a first end 11 of the anterior portion 5 is attached to a superior end 8 of one of the anterior longitudinal posts 3, and a second opposite end 12 of the anterior portion 5 is attached to the other one of the anterior longitudinal posts 3. In a similar way, the posterior portion 6 is interconnecting the superior ends 8 of the posterior longitudinal posts 4, and a first end 13 of the posterior portion 6 is attached to a superior end 8 of one of the posterior longitudinal posts 4, and a second opposite end 14 of the posterior portion 6 is attached to the other one of the posterior longitudinal posts 4.

The lateral portions 7 are interconnecting the inferior ends 9 of the anterior longitudinal posts 3 and the posterior longitudinal posts 4. Thus, each one of the lateral portions 7 extends between an inferior end 9 of one of the anterior longitudinal posts 3 and an inferior end 9 of one of the posterior longitudinal posts 4.

In the embodiment shown in FIG. 1, the mounting slots 2 are arranged in the anterior portion 5 and in the posterior portion 6. The anterior portion 5 comprises four mounting slots 2 and the posterior portion 6 comprises four mounting slots 4. The number of mounting slots 2 arranged in the frame 1 is preferably at least four. The frame 1 has a curved shape which is adapted to the shape of the head. Furthermore, the frame 1 has an outer width w, and the width w is preferably approximately 24 cm.

Figure 2:
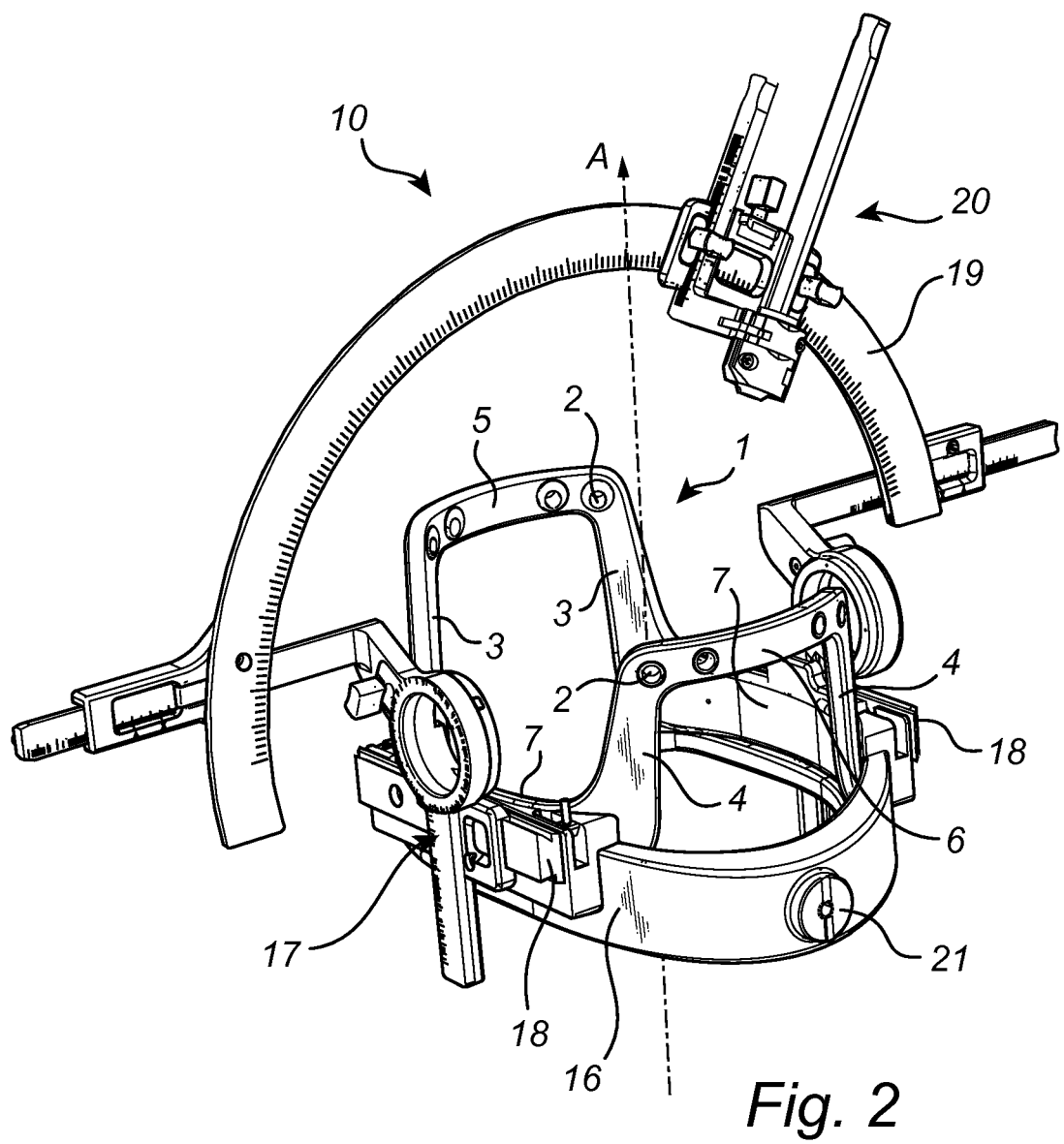
FIG. 2 shows a stereotactic frame system comprising a frame as shown in FIG. 1, according to one embodiment of the present invention.

In FIG. 2 a stereotactic frame system 10 comprising a frame 1, as illustrated in FIG. 1, is shown. The stereotactic frame system 10 comprises a frame docking device 16, and the frame 1 is detachably attached to the frame docking device 16. The stereotactic frame system 10, i.e. the frame docking device 16 of the stereotactic frame system 10, is attached to the lateral portions 7 of the frame 1. Thus, each one of the lateral portions 7 of the frame 1 comprises a fastening device 15 which may be attached to the frame docking device 16. Naturally, each lateral portion 7 may be provided with more than one fastening device 15.

As further seen in FIG. 2, the frame docking device 16 comprises a stereotactic scale 17 and stereotactic scale attachment means 18, and the stereotactic scale 17 is attached to the attachment means 18. The stereotactic frame system 10 comprises a stereotactic arc 19, and a stereotactic arc needle holder 20 is adjustably mounted on the stereotactic arc 19. The frame docking device 16 is further provided with a fixing device 21. The fixing device 21 may be attached to the surgical bed during surgery, such that the stereotactic frame system 10 is fixed during surgery.

As illustrated in FIG. 2, the frame 1 comprises two anterior longitudinal posts 3 and two posterior longitudinal posts 4, extending along a longitudinal axis A. Furthermore, the frame 1 comprises an anterior portion 5, adapted to be arranged at the anterior side of the head, the anterior portion 5 is interconnecting the two anterior longitudinal posts 3, and a posterior portion 6, adapted to be arranged at the posterior side of the head, interconnecting the two posterior longitudinal posts 4. The frame 1, according to the embodiment shown in FIG. 2, comprises eight mounting slots 2 provided in the anterior portion 5 and in the posterior portion 6. The anterior longitudinal posts 3 and the posterior longitudinal posts 4 are interconnected with two lateral portions 7, adapted to extend one on each side of the head. The lateral portions 7 are axially offset, i.e. axially displaced, along the axis A, with respect to the anterior and posterior portions 5, 6. Furthermore, the frame 1 is made from a electromagnetically inert composite material.

In the embodiment illustrated in FIG. 2, the frame 1 is attached to a stereotactic frame system for open surgery. However, the frame 1 may be used with, and attached to, many other types of medical equipments. For example, the frame 1 may be used in radio treatment, therapy (Linac) or surgery (such as with a Gammaknife), or in imaging (MR, CT, X-Ray, PET), or in ultra sound treatment (imaging or surgery), or with laser treatment.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A frame for fixation of equipment to the head of a patient during neurological diagnosis, stereotactic imaging, therapy or surgery, said frame being adapted to enclose the head of the patient, said frame comprising:
   a number of mounting slots arranged in said frame, said mounting slots being adapted to receive a number of fixation pins adapted to fixate said frame to a bone in said head;
   two anterior longitudinal posts and two posterior longitudinal posts, extending along a longitudinal axis A;

an anterior portion, adapted to be arranged at the anterior side of the head, said anterior portion interconnecting said two anterior longitudinal posts; and a posterior portion, adapted to be arranged at the posterior side of the head, said posterior portion interconnecting said two posterior longitudinal posts, wherein said anterior longitudinal posts and said posterior longitudinal posts are interconnected with two lateral portions, adapted to extend one on each side of said head, and wherein said lateral portions are axially offset, along said longitudinal axis A, with respect to said anterior and posterior portion, wherein said anterior portion is adapted to extend superior of eyes of the patient and said lateral portions are adapted to be arranged inferior of ears of the patient, and wherein each one of said anterior and posterior longitudinal posts comprises a superior end and an inferior end, wherein said anterior portion is interconnecting said superior ends of said anterior longitudinal posts.

2. The frame according to claim 1, wherein said posterior portion is interconnecting said superior ends of said posterior longitudinal posts.

3. The frame according to claim 1, wherein said lateral portions are interconnecting said inferior ends of said anterior longitudinal posts and said posterior longitudinal posts.

4. The frame according to claim 1, wherein the anterior portion and the posterior portion are axially offset with respect to each other along said axis A.

5. The frame according to claim 4, wherein the anterior portion is arranged superior of the posterior portion along said axis A.

6. The frame according to claim 1, wherein said anterior portion comprises a number of mounting slots.

7. The frame according to claim 1, wherein said posterior portion comprises a number of mounting slots.

8. The frame according to claim 1, wherein said frame has a curved shape which is adapted to the shape of the head of the patient.

9. The frame according to claim 1, wherein said frame is made from a electromagnetically inert composite material.

10. The frame according to claim 1, wherein each one of said lateral portions comprises at least one fastening device, adapted to detachably attach said frame to a stereotactic frame system.

11. The frame according to claim 2, wherein said lateral portions are interconnecting said inferior ends of said anterior longitudinal posts and said posterior longitudinal posts.

12. The frame according to claim 1, wherein the anterior portion and the posterior portion are axially offset with respect to each other along said axis A.

13. The frame according to claim 2, wherein the anterior portion and the posterior portion are axially offset with respect to each other along said axis A.

14. The frame according to claim 3, wherein the anterior portion and the posterior portion are axially offset with respect to each other along said axis A.

15. The frame according to claim 1, wherein said anterior portion comprises a number of mounting slots.

16. A stereotactic frame system comprising:
the frame according to claim 1; and
a frame docking device,
wherein said frame is detachably attached to said frame docking device.

17. The stereotactic frame system according to claim 16, wherein said frame docking device comprises at least one stereotactic scale.

18. The stereotactic frame system according to claim 17, wherein said frame docking device comprises at least one stereotactic scale attachment device, and wherein said stereotactic scale is attached to said attachment device.

* * * * *